United States Patent [19]

Strecker

[11] Patent Number: 5,207,644
[45] Date of Patent: May 4, 1993

[54] DEVICE WITH IMPLANTABLE INFUSION CHAMBER AND A CATHETER EXTENDING THEREFROM

[76] Inventor: Ernst P. Strecker, Vierordtstrasse 7a, D-7500, Karlsruhe 41, Fed. Rep. of Germany

[21] Appl. No.: 646,763
[22] PCT Filed: May 11, 1989
[86] PCT No.: PCT/DE89/00295
 § 371 Date: Mar. 4, 1991
 § 102(e) Date: Mar. 4, 1991
[51] Int. Cl.$^5$ .............................. A61M 11/00
[52] U.S. Cl. ........................ 604/93; 604/175
[58] Field of Search ............ 604/93, 175, 185, 174, 604/180, 244

[56] References Cited

U.S. PATENT DOCUMENTS

| | | |
|---|---|---|
| 3,971,376 | 7/1976 | Wichterle . |
| 4,710,167 | 12/1987 | Lazorthes ............................ 604/93 |
| 4,718,894 | 1/1988 | Lazorthes ............................ 604/93 |
| 4,778,452 | 10/1988 | Moden et al. .................. 604/175 X |
| 4,802,479 | 2/1989 | Haber et al. . |

FOREIGN PATENT DOCUMENTS

| | | |
|---|---|---|
| 0119596 | 9/1984 | European Pat. Off. . |
| 0233986 | 9/1987 | European Pat. Off. . |
| 0260080 | 3/1988 | European Pat. Off. . |
| 0268108 | 5/1988 | European Pat. Off. . |
| 1812228 | 7/1969 | Fed. Rep. of Germany . |
| 3102993 | 8/1982 | Fed. Rep. of Germany . |
| 3309788 | 10/1984 | Fed. Rep. of Germany . |
| 3837779 | 5/1989 | Fed. Rep. of Germany . |
| 8804914 | 7/1988 | France . |

*Primary Examiner*—John D. Yasko
*Attorney, Agent, or Firm*—Max Fogiel; Richard J. Godlewski

[57] ABSTRACT

There has been provided a catheter system which can be percutaneously implanted through a skin opening and which can be inserted for example by being pushed along a guide wire. An embodiment provides an infusion chamber which can be changed between a condi7 tion of reduced cross-section, upon being inserted, and a position of use which is expanded in relation thereto, in the implanted condition, and which is provided with expandable means which after expansion remain in the expanded condition, for shape retention purposes. The expansion means may be for example a balloon catheter which can be removed after the expansion operation. Another embodiment makes use of an infusion chamber which is of a stiff configuration.

19 Claims, 4 Drawing Sheets

DEVICE WITH IMPLANTABLE INFUSION CHAMBER AND A CATHETER EXTENDING THEREFROM

The invention relates to a device comprising an infusion chamber which is implantable into the subcutaneous fatty tissue of a patient and which has a region of elastic material, which can be pierced by means of an injection needle, and comprising a catheter which extends away from the infusion chamber and which can be introduced into a blood vessel, for example an artery, or another body cavity.

German patent specification No 3 102 993 already discloses a subcutaneously implantable device for the supply of liquid medications which comprises an infusion chamber with a piercable membrane as a puncture window and a hose connected to the chamber for transmission of the medicament. Disposed in opposite relationship to the puncture window is a reinforcement which prevents the rear wall of the chamber from suffering from perforations.

German patent specification No 3 309 788 describes an entirely similar device comprising an infusion chamber having a piercable puncture window, and a catheter which can be connected to the infusion chamber. The infusion chamber which is referred to as a 'injection member' has an annular bead which surrounds the puncture window and which projects beyond same and in opposite relationship to the annular bead at the underside a plate which projects peripherally beyond the chamber, with holes arranged in a distributed array around the periphery, for fixing by means of threads in the implanted condition.

Devices of that kind permit permanent access to a venous or arterial vessel. Devices intended for arterial vessel accesses differ from venous systems by virtue of a valve at the tip of the catheter in order to preclude occlusion due to a reverse flow of blood in the arterial high-pressure system due to thrombosis formation.

Devices of that kind which serve for the selective feed of medicaments into vessels can be subcutaneously implanted, which presupposes surgical intervention at any event with the use of local anaesthetic.

In a known implantation method, after an incision in the skin has been made, the vessel into which a catheter is to be introduced is opened for example by means of a puncture cannula or in another suitable manner and then the catheter is inserted into the vessel. Thereupon an epifascial pocket is to be prepared for the infusion chamber and the infusion chamber is to be placed in the pocket in such a way that a puncture window in the form of a diaphragm lies outside the cut location under the skin. After the implantation operation and after the operation which is possibly carried out beforehand of fitting a suction drainage, the wound is to be closed with subcutaneous or skin sutures.

If for anatomical reasons access to the vessel is possible only at a further distance from the intended position of the infusion chamber, a skin incision must be made in the region of that access and the cathether must be laid from a subcutaneous pocket for receiving the infusion chamber through a subcutaneous tunnel to the skin incision before the catheter can be introduced into the vessel.

Subcutaneously implantable devices are suitable in particular for intra-arterial chemotherapy which permits regional tumourtherapy of primary tumours and metastases. For the purposes of pre-implantation planning, an arteriograph must be produced in order to give precise information about the anatomical vessel supply to a tumour-bearing organ and thus determine the location of the catheter tip in the vessel system for the purposes of medicament delivery.

The advantage of the intra-arterial method is that higher levels of concentration of the chemotherapy agents to be used can be introduced into the tumour tissue, which thus permit specific and directed treatment with lower general side-effects. The medicament which is to be delivered intra-arterially can be delivered only through a puncture in the skin and the diaphragm of the puncture window into the infusion chamber and from there selectively into the tumour-supplying artery by way of the hose or tube system which is introduced into the latter.

However an unsatisfactory aspect in regard to the known catheter systems is that the infusion chamber must be intra-operatively surgically implanted and in positioning of the infusion chamber at a location remote from the vessel access, a further skin incision must be made and the catheter must be laid through a subcutaneous tunnel to the skin incision before it is possible to introduce the catheter into the vessel. That means that a major operation is always necessary, such as for example a laparotomy when dealing with liver tumours, in order to be able precisely to insert the catheter and place the infusion chamber. The strain involved in such an operation is frequently not reasonable for tumour patients as for example in the case of liver metastases of a primary colon carcinoma, the average life expectancy is only about six months.

The object of the invention is therefore to provide a device for the above-indicated purpose, which is less invasive than the subcutaneously implantable systems and which accordingly can be implanted more easily and with less strain on patients.

That object is attained by the device set forth in the classifying portion of claim 1 being in the form of a system which can be implanted percutaneously through a skin puncture opening.

Therefore the device according to the invention is an infusion chamber system in which the infusion chamber does not have to be inserted intra-operatively surgically under the skin in subcutaneous fatty tissue, but implantation is effected percutaneously through a puncture opening in the skin which has been previously enlarged by means of a dilator. In that situation it is possible to use a guide wire which has been previously introduced and the implantation operation can be effected by pushing the infusion chamber over the above-mentioned guide wire, with the infusion chamber being surrounded by an insertion tube which after implantation can be withdrawn towards the side remote from the catheter.

A further development of the invention, which facilitates the percutaneous insertion operation, provides that the infusion chamber is provided with an insertion cone which extends in the insertion direction and which enlarges towards the infusion chamber and which promotes expansion of the skin opening in the step of introducing the infusion chamber.

Desirably the insertion cone may be of a flat shape and in those devices in which the catheter extends away on the side of the insertion cone, the insertion cone may extend in the implanted condition through the subcutaneous fatty tissue to for example an artery so that that arrangement ensures that the infusion chamber is supported with respect to the punctured vessel and provides additional sealing in respect of the puncture hole in the wall of the vessel.

In another development which similarly facilitates percutaneous insertion, the infusion chamber is accommodated in an insertion tube which can be withdrawn after the implantation operation in opposite relationship to the insertion direction.

An important configuration of the invention is characterised in that the infusion chamber is changeable between a condition which is reduced in cross-section and which permits percutaneous insertion by being pushed on over a guide wire, and a position of use in which it is enlarged in comparison therewith (in the implanted condition), and is provided with expandable means which remain in the expanded condition after the expansion operation and which hold the infusion chamber in the expansion position.

An infusion chamber of that kind of configuration can be introduced through the skin for example in the folded-down condition and can be expanded to its position of use after the operation of placing same under the skin by means of suitable steps and means.

For the purposes of intra-arterial chemotherapy, that system may be implanted in combination with the necessary arteriograph for anatomical representation of tumour and tumour-bearing organ, in one session. As that does not require a major operation, in contrast to the subcutaneous implantation of a catheter system, that affords a great deal of relief from the point of view of the patient.

Admittedly German laid-open application (DE-OS) No 18 12 228 already discloses a testicle prosthesis in the form of a hollow body which can be folded down and which in the folded-down condition can be inserted through a minimal incision into the scrotum cavity and which can be filled with a fluid 'in situ' and can thus be expanded into its proper position of use, but that hollow body is held in the expanded condition solely by the fluid filling same and would therefore be totally useless as an infusion chamber. In that respect, in accordance with the invention, the infusion chamber in accordance with the above-indicated configuration is provided with expandable means which remain in the expansion position and permanently prevent collapse of the infusion chamber after the implantation operation.

In the embodiment with an infusion chamber which is reduced in cross-section in the implantation operation, that chamber can be expanded by prestressed spring means which after the release of an arresting means (after the implantation step) spring open into their expansion position and in so doing expand the infusion chamber from its condition of being reduced in cross-section, into its position of use. The above-mentioned prestressed spring means may be spring rings, at least one spring spiral which spreads out itself or at least one spring sleeve, wherein when the spring means are in the form of a spring sleeve, provided in the region of a puncture window is an aperture for opening the window at the inside of the chamber, for sticking in a puncture cannula, or the spring sleeve can be so expanded that formed between the longitudinal slot edges of the spring sleeve in the expansion position is a longitudinal slot which permits a cannula to be stuck in.

In accordance with another development of the invention, the prestressed spring means which are accommodated in the infusion chamber can be held in their prestressed condition by the insertion tube which embraces the infusion chamber and can be released after implantation by withdrawal of the insertion tube and expand the infusion chambe into the proper position of use thereof.

The means for expansion of the infusion chamber however may also be an expandable support sleeve in the form of a wire mesh or wire netting or in the form of an expandable tube, wherein once again provided in the region of the puncture window is an aperture for opening the latter at the inside of the chamber, for the insertion of a puncture cannula.

When the means for expansion of the infusion chamber and for holding same in its expansion position is in the form of a tube, the tube may advantageously be a small thin-walled expandable tube. It has been found advantageous in that respect if the small thin-walled tube is provided with lateral longitudinal slots beside an aperture in the region of the puncture window. On the other hand, longitudinal slots of that kind may not be provided in opposite relationship to the puncture window so that the tube which is closed at that location acts as a cannula stop plate for preventing perforations of the chamber wall which is in opposite relationship to the puncture window.

A development further provides that the slotted tube is expandable by axial stressing and accordingly is provided with a clamping screw which extends in parallel relationship to the longitudinal axis of the tube through same and which bears with its screw head against a transverse leg at one end of the tube while the other end of the screw is screwed into a female screwthread in the region of a transverse leg at the other end of the tube.

In accordance with another development of the above-indicated configuration, accommodated within the infusion chamber is an expandable balloon portion of a balloon catheter, which balloon portion is removable from the chamber in the collapsed condition, and the balloon catheter portion is arranged at least approximately in alignment with the catheter which can be inserted into a vessel, and there are provided means for closing the infusion chamber when the balloon catheter is removed.

In accordance with yet another development of the last-mentioned configuration, accommodated within the infusion chamber is a spreadable spreading portion of a spreading tube, which spreading portion is removable from the chamber in the non-spread condition, and the spreading tube portion is arranged at least approximately in alignment with the catheter which can be inserted into a vessel, and there are provided means for spreading the spreading portion against spring forces returning same, and means for closing the infusion chamber when the spreading tube is removed. The spreading portion of the spreading tube in that construction may desirably comprise limb portions which are separated from each other by longitudinal slots in the peripheral portion of the spreading tube, each limb portion having a respectively outwardly directed curvature, while fixedly connected to the distal end of the spreading tube is a pulling member which sticks out beyond the other end of the spreading tube, for spreading the limb portions outwardly as a result of a spreading force.

The means for closing the infusion chamber upon removal of the balloon catheter or the spreading tube respectively may desirably be a detachable elastic ring which is accommodated in a prestressed condition on the distal shank end of the balloon catheter or the spreading tube respectively and which when the balloon catheter is withdrawn from the infusion chamber remains as a closure plug in and permanently sealingly closes off the opening which hitherto accommodates the balloon catheter or the spreading tube.

The means for closing the infusion chamber however may also be a plug which is accommodated in the above-mentioned chamber opening, with a window through which passes the balloon catheter or the spreading tube and which closes automatically after withdrawal of the balloon catheter or the spreading tube from the infusion chamber.

In accordanc with another important development, the means for expansion of the infusion chamber may also comprise a memory alloy which experiences a predetermined change in configuration under the effect of heat and in so doing expands the infusion chamber into the position of use thereof. The expansion means comprising a memory alloy may involve a wire spiral which under the effect of heat can be put into its proper expansion condition, or a rolled-up plate which is arranged in opposite relationship to a puncture window in the infusion chamber and which is adapted to unroll under the effect of heat and which serves in the unrolled condition as a cannula stop plate.

Desirably, the infusion chamber may be a hollow body which is flat in the expanded condition after implantation, with a puncture window disposed in one of the chamber walls forming the flat sides of the chamber, while associated with the other chamber wall in opposite relationship to the puncture window is a cannula stop plate for providing protection from perforations.

The configuration with an infusion chamber of a fixed shape is extremely simple in terms of structure and after the implantation operation does not require any further manipulations in order to put the infusion chamber into its proper position of use.

In accordance with a further development, the puncture window may be a plug which comprises silicone or a similar material and which closes off the infusion chamber relative to the exterior and which is accommodated in a prestressed condition in a portion of the infusion chamber. Desirably the puncture window may be disposed in the region of an aperture which passes through the chamber wall and which after implantation lies under the skin of the patient and accordingly permits substantially 'perpendicular' puncturing.

It has been found equally advantageous if integrated into the outside zone of the material forming the puncture window is a grid which consists of suitable strong material and which prevents the prestressed window material from yielding.

Further in accordance with a development, the puncture window may have extending therearound an edge bead which projects beyond the puncture window on the outside of the chamber and which can be felt through the skin of the patient and which accordingly facilitates puncturing of the infusion chamber.

Still a further development provides that the infusion chamber and the catheter are separably connected together by means of a plug connection. That configuration permits extremely simple implantation by a procedure such that firstly the catheter is introduced by way of a previously inserted guide wire into for example a vessel to be punctured, and is then joined to the infusion chamber which previously or also thereafter has been implanted into a tunnel introduced from the puncture point into the subcutaneous fatty tissue of a patient.

In accordance with a further feature of the invention, particularly advantageous positional stabilisation of the infusion chamber after implantation thereof can be achieved when the infusion chamber is provided with resilient anchorage means which extend away from the chamber wall on the outside thereof and which are disposed on the underside—in the implanted condition—and possibly on the end walls of the infusion chamber and which engage into the subcutaneous fatty tissue surrounding the chamber. Such anchorage means may equally be provided in relation to an infusion chamber which is stable in shape and variable in cross-section.

The anchorage means may comprise anchor pins which in the position of use project on the outside from the wall of the infusion chamber or loops whose ends are each connected to the chamber wall. In regard to such anchorage means, it has been found advantageous if as an implantation aid the infusion chamber is accommodated in an outer casing which can be stripped off after the implantation operation, and the anchorage means are applied against the chamber wall by means of the outer casing. After removal of the outer casing, the anchorage means then spread out and provide for precise positional stabilisation of the infusion chamber so that the infusion chamber cannot yield laterally nor move in the longitudinal direction, in the puncture procedure.

Some embodiments of the device according to the invention and the proper use thereof will now be described in greater detail with reference to the accompanying diagrammatic drawings in which.

Figure 1:
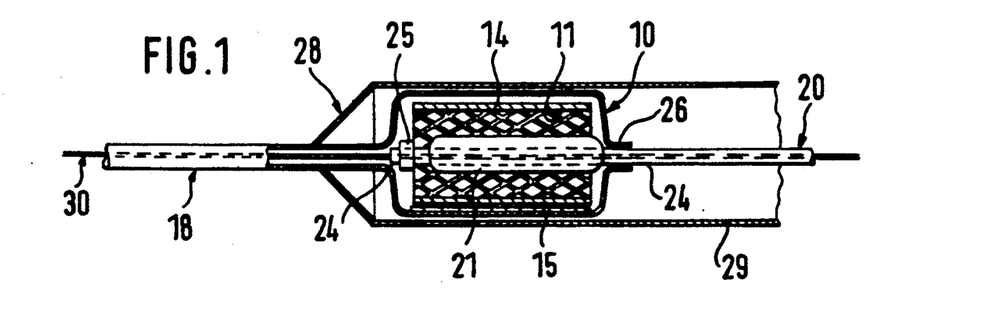
FIG. 1 is a view on a greatly enlarged scale of an infusion chamber with a balloon catheter for expansion purposes, which is removable after implantation.
Figure 2:
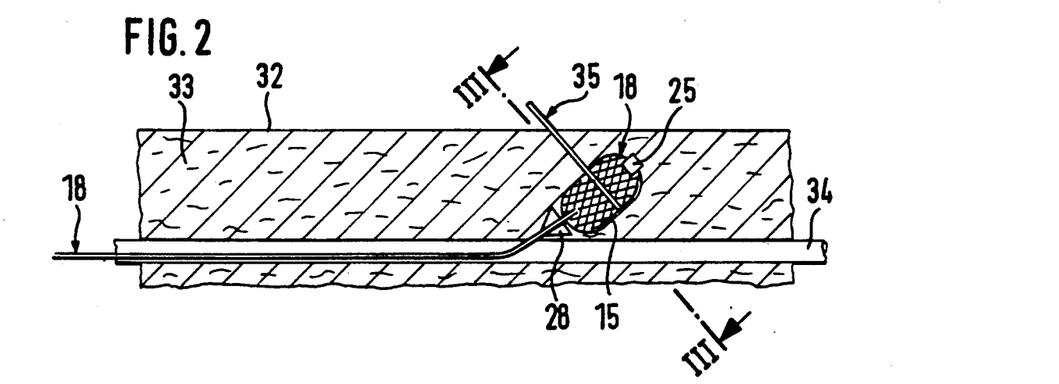
FIG. 2 is a view on a reduced scale in comparison with FIG. 1 of the device when properly used after implantation with an infusion chamber which is accommodated in tissue near the skin, and a catheter which extends away from the infusion chamber and which is introduced into a vessel.
Figure 3:
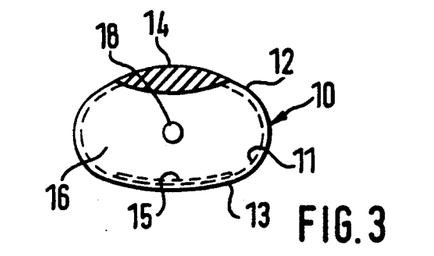
FIG. 3 is a view on an enlarged scale and in cross-section taken along line III—III in FIG. 2 through the infusion chamber when expanded in the proper fashion.

The device shown in particular in FIG. 1 comprises an elongated infusion chamber 10 of expandable material, which is changeable between the condition shown in FIG. 1, of reduced cross-section, and the expansion position shown in FIGS. 2 and 3 after implantation. Disposed within the infusion chamber 10 is an expansible support sleeve 11 of expansible mesh or netting, which extends substantially over the entire length of the infusion chamber and which internally supports the chamber walls in the expanded condition.

In the expanded condition the infusion chamber 10 is approximately in the configuration of a flattened ellipsoid with the chamber walls 12, 13 forming the flat sides of the chamber. Disposed in the one chamber wall 12 is a puncture window 14 in the form of a diaphragm which is thick in comparison with the chamber walls and which is not expansible but which can be pierced without difficulty by means of an infusion cannula and which is of such a nature that after removal of the puncture cannula, the puncture opening automatically closes again. A metal plate 15 for providing protection from needle perforations is associated internally with the chamber wall 13 forming the other flat side of the chamber, in opposite relationship to the puncture window 14.

Connected to the infusion chamber 10 at the one end thereof is a catheter 18 which communicates with the interior 16 of the chamber and which is a tube or hose system which can be introduced into an artery, a vein or other body cavity. The device further includes a balloon catheter 20 which is inserted with its balloon portion 21 into the infusion chamber through an opening 22 which is aligned with the catheter 18 which can be inserted into a vessel. The balloon portion 21 of the balloon catheter 20 extends substantially over the entire length of the support sleeve 11 which is accommodated in the infusion chamber and a detachable sealing plug 25 is accommodated at the distal end on the shank 24 of the balloon catheter. The insertion opening 22 of the infusion chamber for the balloon catheter 20 has a peripherally extending sealing ring 26 which is closed in a manner still to be described hereinafter upon removal of the balloon catheter from the infusion chamber, by means of the sealing plug 25 which is carried on the distal end of the shank of the balloon catheter.

In addition the device is provided with a cone 28 which is disposed on the side of the infusion chamber which faces towards the catheter 18 which can be introduced into a vessel, and the infusion chamber is enclosed by an insertion tube 29 which extends away from the insertion cone 28 in the same direction as the balloon catheter 20. The cone 28 facilitates percutaneous insertion. The insertion tube 29 can be removed after implantation by withdrawal in the direction of the balloon catheter. Finally FIG. 1 also shows a guide wire 30 which extends through the balloon catheter 20 with the balloon portion 21, the infusion chamber 10 and the catheter 18 which can be inserted into a vessel.

The device shown in FIG. 1 of the drawing is percutaneously implanted in proper use thereof. For that purpose, using the Seldinger procedure and accordingly in known manner, firstly the vessel to be provided with a catheter is punctured and the guide wire 30 is inserted into the vessel through the puncture cannula. The catheter 18 which is intended to be inserted into the vessel is then pushed on to the guide wire 30 and progressively introduced into the vessel, preferably with X-ray monitoring. In the same manner, the infusion chamber 10 which is enclosed by the insertion tube 29, in its condition involving a reduced cross-section as shown in FIG. 1, is inserted through the skin incision afforded by the above-mentioned puncture cannula, and is implanted in the correct position in near-subcutaneous fatty tissue in such a way that the infusion window 14 is under the skin. In that situation the cone 28 which is disposed in front of the infusion chamber 10 in the insertion direction serves as an aid for expansion of the puncture opening in the skin of the patient, which forms the location for insertion of the infusion chamber. After insertion of the catheter 18 and positioning of the infusion chamber 10 in the correct position, the insertion tube 29 and the guide wire 30 are pulled back towards the side away from the catheter 18. In that situation the implanted infusion chamber 10 must be held in position by means of a suitable retaining device (not shown).

The next following step in the implantation procedure then lies in expansion of the infusion chamber 10 into its position of use, by the balloon portion 21 accommodated within the infusion chamber being supplied with pressure medium in known manner through a lumen of the balloon catheter 20, and expanded thereby. As a result of expansion of the balloon portion 21, the inner support sleeve 11 of the infusion chamber is subjected to permanent enlargement which in turn enlarges the infusion chamber which comprises expansible material. When that happens the infusion chamber displaces the tissue surrounding it.

Expansible sleeves of wire mesh or netting which remain in their expansion position after the expansion step are known so that there is no need for a description in that respect.

After expansion of the inner support sleeve 11 and thus the infusion chamber 10, the supply of pressure medium to the balloon portion 21 of the balloon catheter 20 is stopped so that the balloon portion collapses. Then, with the balloon portion 21 in the collapsed condition, the balloon catheter is withdrawn from the infusion chamber by way of the opening 22 provided with the sealing ring 26. When that is done, the detachable plug 25 arranged on the distal end 24 of the shank of the balloon catheter remains caught in the sealing ring 26 of the above-mentioned opening 22, and permanently sealingly closes it off relative to the exterior. After the infusion chamber 10 with the catheter 18 extending away therefrom has been properly positioned, the guide wire 30 can be withdrawn, more particularly before or after withdrawal of the balloon catheter 20. At any event, the through opening in the closure plug 25 closes automatically; finally the closure plug 25 is received in the sealing ring 26 and permanently sealingly closes off the infusion chamber.

The particular advantage of the device according to the invention is that, in contrast to subcutaneous systems, this system can be implanted percutaneously through an opening in the skin, thus involving much lower levels of patient stress than when using known systems.

FIG. 2 diagrammatically illustrates the implanted condition. The expanded infusion chamber 10 is accommodated in the subcutaneous fatty tissue 33, with the puncture window 14 lying under the skin 32. The opening 22 in the infusion chamber 10, through which the balloon catheter 20 extends during the implantation step, is closed by means of the plug 25 which was detachably carried on the distal end 24 of the shank of the balloon catheter and which, upon withdrawal of the collapsed balloon portion 21 from the infusion chamber 10, moved into its closure position in the opening 22. The catheter 18 which communicates with the interior 16 of the infusion chamber 10 is inserted into a blood vessel 334 which may be an artery or a vein. The cone 38 for facilitating percutaneous implantation bears against the outside wall of the vessel 34. The cone 28 can be of a flat configuration and can extend into the artery 34, that is to say it can provide an additional sealing effect in relation to the puncture hole in the wall of the artery. FIG. 2 further indicates a puncture needle 35 which is inserted into the infusion chamber 10 for the purposes of medicament delivery through a puncture in the puncture window 14 and the tip of which bears against the metal plate 15 which is disposed in opposite relationship to the puncture window 14. After withdrawal of the puncture needle, the puncture opening in the diaphragm of the puncture window closes automatically.

Figure 4:
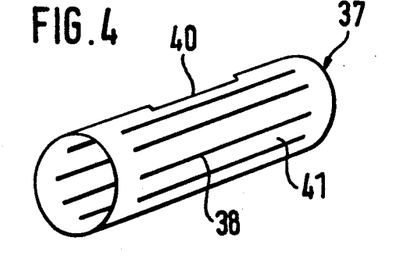
FIG. 4 is a perspective view of a small slotted tube in the non-expanded condition as a support sleeve for maintaining the shape of the infusion chamber after expansion thereof.
Figure 5:
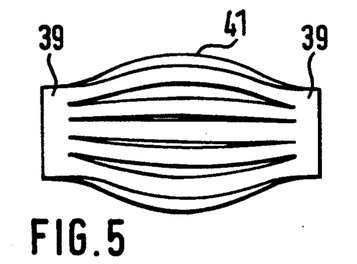
FIG. 5 is a side view of the slotted tube shown in FIG. 4 in the expanded condition.

Instead of a support sleeve in the form of a wire mesh or netting, an expandable tube 37 in the form of a small thin tube provided with longitudinal slots 38, as shown in FIG. 4, may also be provided within the infusion chamber. The longitudinal slots extend between collars 39 at the ends of the tube and provided on one side in the wall of the tube is an aperture 40 associated with the puncture window. FIG. 5 shows the support sleeve in the form of a slotted tube in the expansion position in which the longitudinal limb portions 41 which extend between the annular collars 39 at the ends of the tube are deformed radially outwardly and are thus suitable for bearing internally against the walls of the infusion chamber.

Figure 6:
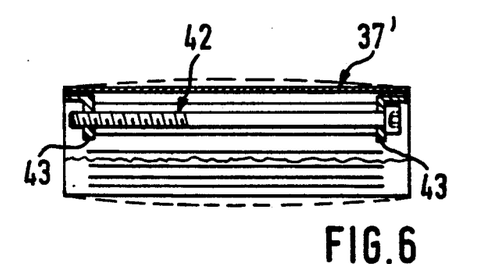
FIG. 6 is a view in longitudinal section of another embodiment of a slotted tube with a clamping screw extending through same.

FIG. 6 is a view in longitudinal section of an embodiment of the small slotted tube 37' with a clamping screw 42 which extends axially through same and which bears with its screw head against an end transverse leg 43 while the screwthreaded portion thereof is screwed into a screwthreaded hole in a transverse leg 43 at the other end of the small tube. The longitudinal limb portions of this embodiment have a slight outward curvature (as shown in broken lines) and can be expanded in the manner shown in FIG. 5 by tightening of the clamping screw 43, the head of which is provided with a wrench engagement surface.

Figure 7:
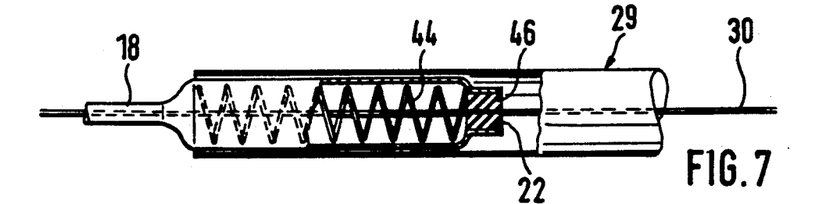
FIG. 7 is a view similar to that shown in FIG. 1 and partly in longitudinal section through a catheter system comprising a spring spiral which is in a spring prestressed condition, as a means for expansion of the infusion chamber.
Figure 8:
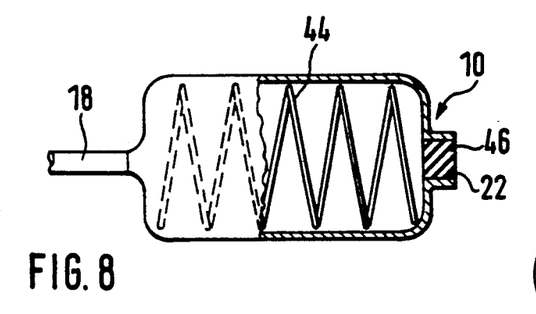
FIG. 8 is a view similar to that shown in FIG. 7 of the infusion chamber with catheter connected thereto after expansion by means of the spring spiral.
Figure 9:
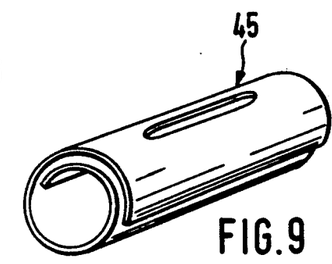
FIG. 9 is a perspective view of a prestressed and self-expanding spring sleeve as a means for expansion of the infusion chamber.
Figure 10:
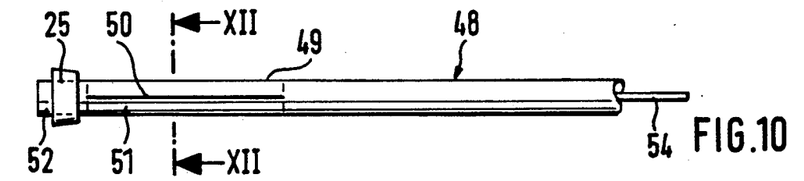
FIG. 10 is a view on an enlarged scale of a spreading tube, in itself, with a detachable ring accommodated on its distal end as a closure plug.
Figure 11:
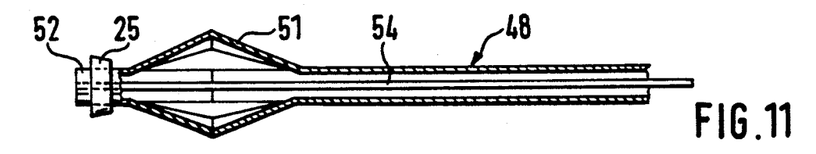
FIG. 11 is a view in longitudinal section of the spreading tube with partially spread spreading portion.
Figure 12:
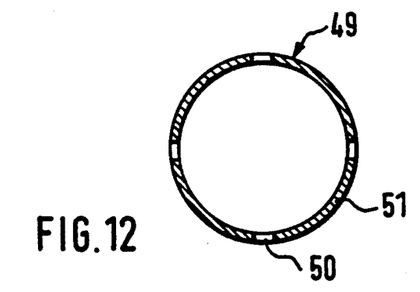
FIG. 12 is a view on a greatly enlarged scale and in cross-section taken along line XII—XII in FIG. 10, through the spreading portion.

As an alternative to the balloon catheter which is shown in FIG. 1 as a means for expansion of the infusion chamber however, it is also possible to provide a spring spiral 44 which is accommodated within the infusion chamber, as shown in FIG. 7, or a spring sleeve 45, as shown in FIG. 9, which is radially compressed and which is held in that prestressed position by means of the insertion tube 29 which can be withdrawn after the implantation step towards the side away from the catheter 18. The opening 22 in the infusion chamber 10 is closed by means of a closure plug 46 of for example silicone, through which the guide wire 30 extends. After withdrawal of the guide wire 30, the perforation in the closure plug 46 closes automatically. FIG. 8 shows the infusion chamber when expanded in the position of use.

The spring spiral 44 shown in FIGS. 7 and 8 and/or the spring sleeve 45 shown in FIG. 9 may also comprise memory metal, in which case it does not need to be held in the compressed position by means of a casing member which can be withdrawn. When said means comprise memory metal, the change into the expansion position takes place under the effect of temperature, that is to say for example by introducing into the infusion chamber a heated fluid which can be removed again after expansion has occurred.

Also as an alternative to the balloon catheter used in FIG. 1 as a means for expansion of the infusion chamber, it is also possible to use a spreading tube 48 which, in normal use, projects with a spreading portion 49 into the infusion chamber 10, instead of the balloon portion 21 of the balloon catheter 20. The spreading portion 49 is disposed in the vicinity of the distal end of the spreading tube 48 and comprises four limb portions 51 which are separated from each other in the peripheral direction by longitudinal slots 50 and which may have an outwardly directed slight preliminary curvature or which may have a bending edge at their ends and possibly at the centre of their longitudinal extent.

Fixedly connected to the distal end 52 of the spreading tube 48 is a pulling means 54 which extends through the spreading tube 48 and which projects beyond the other end thereof. When the spreading tube 48 is otherwise held fast, the limb portions 51 of the spreading portion are spread out in the manner shown in FIG. 11 by means of the pulling member 54. When the pulling force which causes spreading movement of the limb portions of the spreading portion is removed, the limb portions move back substantially into their initial position of their own accord and in that condition the spreading tube can be withdrawn from the infusion chamber in a similar manner to the balloon portion of the balloon catheter. In that operation the sealing plug 25 carried on the distal end 52 of the spreading tube remains behind in the corresponding opening of the infusion chamber, and closes off the opening.

Figure 13:
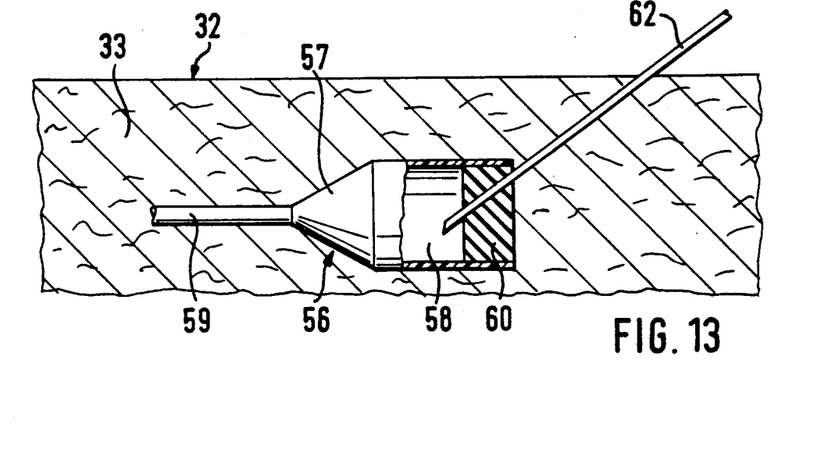
FIG. 13 is a view in longitudinal section of part of a catheter system with an infusion chamber of fixed shape, in the implanted condition.
Figure 14:
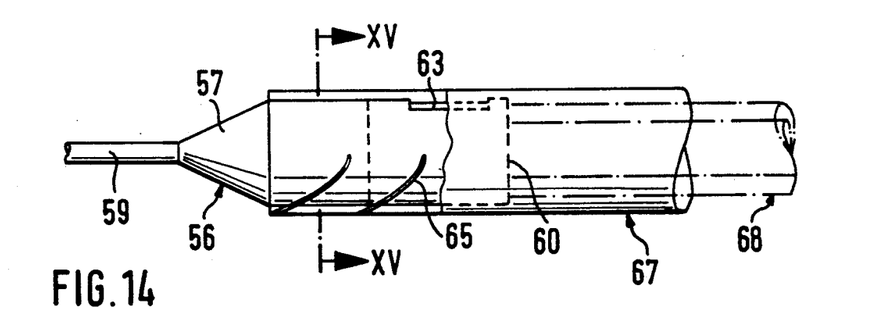
FIG. 14 shows an embodiment which is modified in comparison with FIG. 13, with a closure plug inserted in the region of an end of the infusion chamber, with a puncture window passing through the chamber wall, and with anchorage means arranged at the underside of the chamber.
Figure 15:
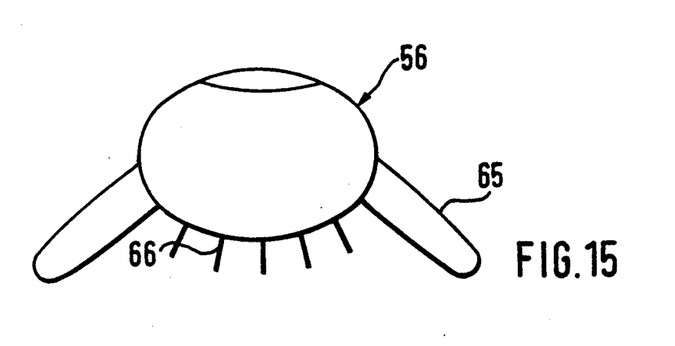
FIG. 15 is a view in cross-section taken along line XV—XV in FIG. 14 through the infusion chamber with released anchorage means.

The systems shown in FIGS. 13 through 15 differ from the above-described systems in that the infusion chambers 56 are of such a configuration as to afford a stable shape and comprise plastic material which is compatible with tissue.

In these embodiments the infusion chamber 56 is closed off at one end by an insertion cone 57. A catheter 59 which can be inserted into a vessel and which communicates with the interior 58 of the infusion chamber extends away from the insertion cone 57. At the other end the infusion chamber is closed by means of a closure plug 60 in the form of a strong silicone plate, which is fitted into the chamber.

The systems shown in FIGS. 13 through 15 are implanted in the same manner as the systems described above, in that firstly a guide wire is introduced through a skin puncture opening for example into an artery, in a procedure which is of no further interest in the present context, and then the catheter with the infusion chamber is pushed over the guide wire, with the guide wire extending through the catheter, the infusion chamber and the closure plug 60 which closes the infusion chamber on the side remote from the catheter. After the operation of placing the infusion chamber in the correct position, the guide wire is retracted in known manner, with the through opening in the closure plug of silicone or other suitable material, which closes off the infusion chamber at the rear side thereof, automatically closing.

FIG. 13 shows the system having an infusion chamber 56 of a fixed shape, similar to the view shown in FIG. 2, in the implanted condition under the skin 32 in the subcutaneous fatty tissue. A puncture in the infusion chamber, for example for the purposes of supplying medicament, is produced in a simple fashion by using an injection needle 62 to pierce the skin 32 and the closure plug 60 which closes off the infusion chamber at the rear end thereof; the injection location automatically closes again after withdrawal of the injection needle. That is shown diagrammatically in FIG. 13.

In the embodiment illustrated in FIG. 14 on the other hand, provided in the chamber wall is an aperture 63 as a puncture window, through which an injection needle can be inserted into the chamber, for piercing the closure plug 60. The embodiment shown in FIG. 14 differs from the embodiment shown in FIG. 13 in that the outside wall of the underside of the chamber, as shown in FIG. 15, is provided with anchorage loops 65 which can be laid over and/or with anchorage pins 66 which can be laid over, and that said anchorage means are pressed against the chamber wall in a forwardly directed direction (in the direction of insertion) by an insertion tube 67 which encloses the infusion chamber 56 and which can be withdrawn towards the side which is closed off by means of a closure plug.

After the implantation step, the insertion tube 67 is withdrawn towards the side remote from the insertion cone, whereupon the anchorage means which are applied against the wall of the chamber during the implantation step stand up in the manner shown in FIG. 15 and penetrate into the subcutaneous fatty tissue of the patient, adjacent the underside of the chamber. That provides for thoroughly desirable positional stabilisation for the infusion chamber. During the operation of withdrawing the insertion tube 67 from the infusion chamber, the latter must be held in its proper position by means of a retaining device 68 as shown in dash-dotted lines in FIG. 14.

Figure 16:
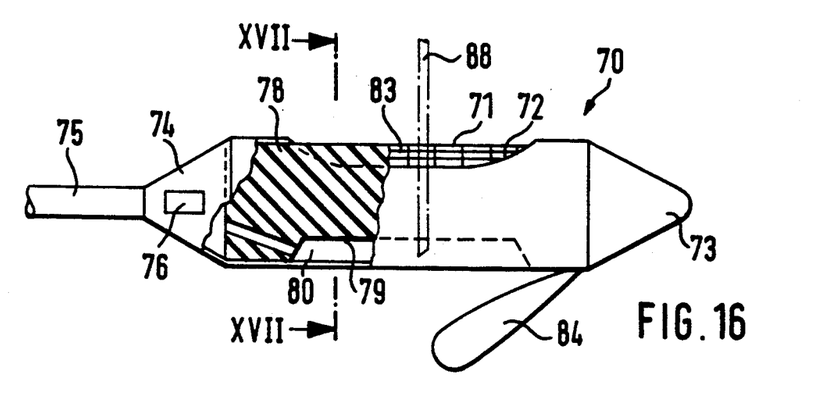
FIG. 16 is a view similar to that shown in FIG. 14 of a further embodiment with an infusion chamber of fixed shape.

In the embodiment shown in FIG. 16, the infusion chamber 70 is of a fixed shape and is in the form of an elongated sleeve portion with an aperture 75 which extends through the peripheral portion of the sleeve, to form a puncture window 71. At one end the peripheral portion of the sleeve is closed by an insertion cone 73 which is formed thereon while at the other end a catheter 75 extends away from an also approximately conical portion 74. The catheter 75 is fixedly or also separably connected to the infusion chamber by way of a plug connection (not shown). The end part of the peripheral portion of the sleeve which is towards the catheter, is also provided with a depression 76 to permit secure engagement of forceps or a clamp. Accommodated within the peripheral portion of the sleeve in a radially prestressed condition is a silicone plug 78 which extends between the two end cone configurations and which fully fills up the sleeve in the region of its two ends while however being flattened off at 79 on the side which is in opposite relationship to the aperture 72 in the peripheral portion of the sleeve, which forms the puncture window 71, thereby forming an internal space 80 which can be punctured through the silicone plug 78, for receiving an infusion solution or a medicament. A duct 82 which opens in the end portion 74 of the sleeve, which is towards the catheter, extends through the silicone plug from the receiving space 80. At least in the region of the aperture forming the puncture window, the silicone plug is provided with a grid 83 which is integrated into its surface and which comprises a thread material which is of a fixed shape, to prevent radial yielding or deflection of the silicone plug in the region of the above-mentioned aperture. Finally, in the same manner as already described above with reference to FIGS. 14 and 15, arranged on the peripheral portion of the sleeve on the outside thereof, at the side remote from the catheter, are anchors 84 in the form of loops which spread out in the implanted condition and which after implantation ensure that the infusion chamber is securely fixed in the subcutaneous fatty tissue of a patient.

Figure 17:
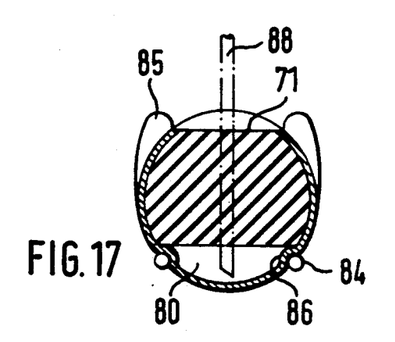
FIG. 17 is a view in section taken along line XVII—XVII in FIG. 16, showing a further modified embodiment of an infusion chamber of fixed shape.

In the embodiment shown in FIG. 17 in a cross-section taken along section line XVII—XVII in FIG. 16, the peripheral portion of the sleeve which forms the infusion chamber 70 is of an approximately oval shape while in the region of the aperture 72 forming the puncture window in the sleeve beads 85 extend on both sides of the opening 72 and project above the puncture window 71. In the implanted condition, the beads 85 permit the position of the puncture window to be felt, through the skin of the patient. On the side which is remote from the puncture window and which in the implanted condition, relative to the skin of a patient, forms the underside of the infusion chamber, the peripheral portion of the sleeve has longitudinally extending inwardly shaped portions 86 which receive the anchor loops 84 which are applied against the wall of the infusion chamber in the implantation operation and which at the same time form a support at the underside for the silicone plug 78 which is accommodated within the sleeve.

When the infusion chamber is punctured, the silicone plug 78 is pierced through the puncture window 71 by means of a cannula 88 which is indicated in FIGS. 16 and 17. After withdrawal of the cannula, the pierced location automatically closes up again, in view of the prestressing of the silicone material, so that the deposit of medicament can be refilled at any time, but medicaments deposited in the receiving space 80 can only flow away by way of the catheter.

Figure 18:
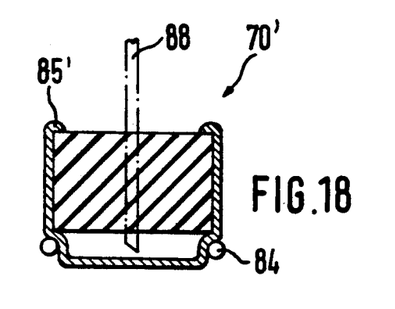
FIG. 18 is a sectional view similar to that shown in FIG. 17 of a cross-sectional configuration, which is alternative to the latter, of an infusion chamber which is of a fixed shape.
Figure 19:
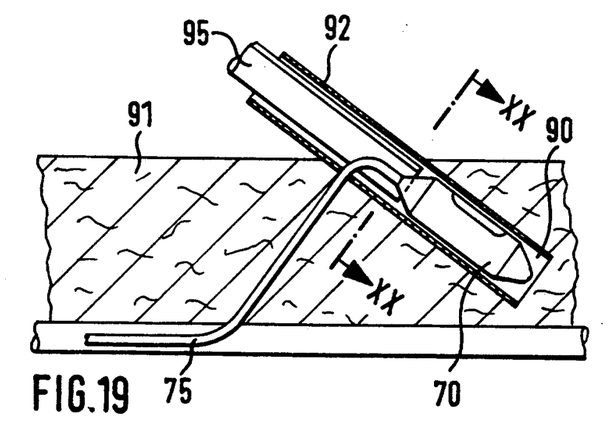
FIG. 19 is a view on a reduced scale of the device illustrated in FIG. 16, in proper use thereof, with a catheter already inserted into a blood vessel and with the infusion chamber during insertion into a tunnel extending away from a skin puncture location.

FIG. 18 is a view similar to that shown in FIG. 17 illustrating an alternative configuration with an infusion chamber 70' which is of substantially rectangular cross-section and which is likewise provided with anchorage means 84' (which are only indicated), being anchorage loops, arranged in the region of the end remote from the catheter. In this embodiment also, extending on both sides of the infusion window 71' and projecting therebeyond are beads 85' which permit the position of the infusion window to be felt through the skin of a patient.

Figure 20:
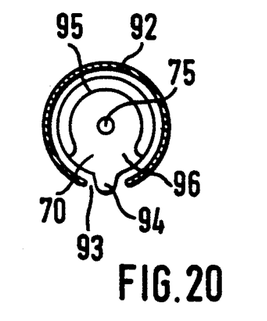
FIG. 20 is a view in cross-section taken along line XX—XX in FIG. 19 through the infusion chamber and a slotted insertion tube which is introduced into the tunnel in the subcutaneous fatty tissue of a patient.

Finally, on a greatly reduced scale in comparison with FIGS. 16 through 18, FIG. 19 shows the implantation of an infusion chamber 70 of that kind, of which one end is connected to a catheter 75 which has already been inserted into a vessel. In that case the infusion chamber is inserted into a chamber 90 which is enlarged from a skin puncture location by means of a dilator (not shown), in the subcutaneous fatty tissue 91 of a patient, with the end thereof which is remote from the catheter, with the insertion operation being facilitated by the insertion cone 73 at the end of the infusion chamber which is remote from the catheter. In that case, as an insertion aid, a slotted insertion tube 92 is pushed into the chamber 90 through the enlarged skin puncture opening and then the infusion chamber is inserted through the insertion tube 92, in which case the catheter connected to the infusion chamber extends through the longitudinal slot 93 in the insertion tube. Desirably, as shown in FIG. 20, the infusion chamber 70 may be provided on the side remote from the puncture window 71 with a longitudinal rib 94 which then engages into the longitudinal slot 93 in the insertion tube 92 and thus provides for correct positioning of the infusion chamber. A further insertion aid is a pusher 95 which is provided with a longitudinal slot 96 in a corresponding fashion to the longitudinal slot 93 of the insertion tube 92 and by means of which the infusion chamber which is connected to the catheter can be pushed through the insertion tube 92 into the prepared receiving chamber 90. After correct positioning of the infusion chamber, firstly the insertion tube 92 and then the pusher 95 are successively withdrawn, whereupon all that is required is closure of the skin puncture opening for concluding the implantation procedure.

The embodiments described with reference to FIGS. 16 through 20 therefore also provide for percutaneous implantation without major surgical intervention.

I claim:

1. A device comprising an infusion chamber which is implantable into the subcutaneous fatty tissue of a patient and which has region of elastic material, which can be pierced by means of an injection needle, and comprising a catheter which extends away from the infusion chamber and which can be introduced into a blood vessel, for example an artery, or another body cavity, characterised by the configuration in the form of a system which is implantable percutaneously with an insertion tube through a skin puncture opening.

2. A device as set forth in claim 1 characterised in that the infusion chamber (10, 56, 70, 70') is provided with an insertion cone (28, 57, 73) which extends in the insertion direction and which enlarges towards the infusion chamber.

3. A device as set forth in claim 1 characterised in that the infusion chamber (10, 56, 70) is accommodated in an insertion tube (29, 67, 92) which after the implantation operation can be withdrawn in opposite relationship to the insertion direction.

4. A device comprising an infusion chamber which is implantable into the subcutaneous fatty tissue of a patient and which has a region of elastic material, which can be pierced by means of an injection needle, and comprising a catheter which extends away from the infusion chamber and which can be introduced into a blood vessel, for example an artery, or another body cavity, characterised in that the infusion chamber (10) is changeable between a condition which is reduced in cross-section and which permits percutaneous insertion for example by being pushed on over a guide wire (30), and a position of use in which it is expanded in comparison therewith (in the implanted condition), and is provided with expandable means (11, 44, 45) which remain in the expanded condition after the expansion operation and which hold the infusion chamber in the expansion position.

5. A device as set forth in claim 4 characterized in that the means for expansion of the infusion chamber (10) are in the form of prestressed spring means (11, 44, 45) which after release of an arresting means (after the implantation operation) spring out into their expansion position and in so doing expand the infusion chamber (10) from its condition of being reduced in cross-section, into its position of use.

6. A device as set forth in claim 5 characterised in that the prestressed spring means are spring rings, at least one spring spiral (44) which spreads out itself, or at least one spring sleeve (45), wherein when the spring means are in the form of a spring sleeve, provided in the region of a puncture window (14) is an aperture for opening the window at the inside of the chamber, for sticking in a puncture cannula, or the spring sleeve can be so expanded that formed between the longitudinal edges of the spring sleeve in the expansion position is a longitudinal slot which permits a cannula to be stuck in.

7. A device as set forth in claim 4 characterised in that the prestressed spring means (11, 44, 45) which are accommodated in the infusion chamber (10) are held in their prestressed position by the insertion tube (29) and are released after implantation by withdrawal of the insertion tube and expand the infusion chamber into the proper position of use thereof.

8. A device as set forth in claim 4 characterised in that the means for expansion of the infusion chamber are an expandable support sleeve (11) in the form of a wire mesh or wire netting or in the form of an expandable tube (37), wherein provided in the region of the puncture window (14) is an aperture (41) which opens the latter at the inside of the chamber, for sticking in a puncture cannula.

9. A device as set forth in claim 8 characterised in that accommodated within the infusion chamber (10) is an expandable balloon portion (21) of a balloon catheter (20), which balloon portion is removable from the chamber in the collapsed condition, and the balloon catheter portion is arranged at least approximately in alignment with the catheter (18) which can be inserted into a vessel, and that means are provided for closing the infusion chamber when the balloon catheter is removed.

10. A device as set forth in claim 9 characterised in that the means for closing the infusion chamber (10) upon removal of the balloon catheter (20) or the spreading tube (48) respectively is a detachable elastic ring (25) which is accommodated in a prestressed condition on the distal shank (24, 52) thereof and which when the balloon catheter or the spreading tube is withdrawn from the infusion chamber remains as a closure plug in and sealingly closes off the opening (22) which hitherto accommodates the balloon catheter or the spreading tube.

11. A device as set forth in claim 9 characterised in that the means for closing the infusion chamber (10) is a plug which is accommodated in the chamber opening (22) and which has a window through which passes the balloon catheter (20) or the spreading tube (48) and which closes automatically after withdrawal of the balloon catheter or the spreading tube from the infusion chamber.

12. A device as set forth in claim 4 characterised in that the means (11, 44, 45) for expansion of the infusion chamber (10) comprise a memory alloy.

13. A device as set forth in claim 12 characterised in that the means for expansion of the infusion chamber (10) comprise a wire spiral (44) which under the effect of heat can be put into its proper expansion condition.

14. A device as set forth in claim 4 characterised in that the infusion chamber (10) is a hollow body which is flat in the expanded condition after implantation and that the puncture window (14) is disposed in one of the chamber walls forming the flat sides of the chamber while associated with the other chamber wall in opposite relationship to the puncture window is a cannula stop plate (15) for providing protection from perforations.

15. A device as set forth in claim 14 characterised in that the infusion chamber (10) in the position of use (after implantation) is approximately in the shape of a flattened ellipsoid.

16. A device as set forth in claim 1 characterised in that the infusion chamber (56, 70) is in the form of an elongate hollow body of fixed shape, from which extends the catheter (59, 75) which can be inserted into a vessel or another body cavity, the elongate hollow body having a puncture window (60, 71) comprising a prestressed piercable material which automatically closes the piercing location again.

17. A device as set forth in claim 16 characterised in that the puncture window involves a plug (60, 78) which comprises silicone or a similar material and which closes off the infusion chamber relative to the exterior and which is accommodated in a prestressed condition in a portion of the infusion chamber.

18. A device as set forth in claim 16 characterised in that the puncture window (71) is arranged in the region of an aperture which passes through the chamber wall.

19. A device as set forth in claim 16 characterised in that integrated into the outside zone of the material forming the puncture window (71) is a grid (83) of strong thread material which prevents the prestressed window material from yielding.

* * * * *